(12) United States Patent
Blake et al.

(10) Patent No.: US 12,050,156 B2
(45) Date of Patent: Jul. 30, 2024

(54) SEALING DEVICE AND METHOD FOR DETECTING A POSSIBLE GAS LEAK AT A FITTING CONNECTION FOR BIOPHARMACEUTICAL PRODUCT

(71) Applicant: SARTORIUS STEDIM FMT SAS, Aubagne (FR)

(72) Inventors: Florian Blake, Aubagne (FR); Frederic Bazin, Aubagne (FR); Shahmir Fatherazi, Göttingen (DE); Michael Braun, Göttingen (DE); Nicolas Thevenin, Aubagne (FR); Marc Hogreve, Göttingen (DE)

(73) Assignee: SARTORIUS STEDIM FMT SAS, Aubagne (FR)

( * ) Notice: Subject to any disclaimer, the term of this patent is extended or adjusted under 35 U.S.C. 154(b) by 0 days.

(21) Appl. No.: 18/556,235

(22) PCT Filed: Apr. 14, 2022

(86) PCT No.: PCT/EP2022/060143
§ 371 (c)(1),
(2) Date: Oct. 19, 2023

(87) PCT Pub. No.: WO2022/223476
PCT Pub. Date: Oct. 27, 2022

(65) Prior Publication Data
US 2024/0192078 A1 Jun. 13, 2024

(30) Foreign Application Priority Data
Apr. 19, 2021 (EP) .................................... 21169252

(51) Int. Cl.
*G01M 3/00* (2006.01)
*F16J 15/02* (2006.01)
(Continued)

(52) U.S. Cl.
CPC .......... *G01M 3/223* (2013.01); *F16J 15/022* (2013.01); *G01N 33/0009* (2013.01)

(58) Field of Classification Search
CPC .... F16J 15/022; G01M 3/223; G01N 33/0009
See application file for complete search history.

(56) References Cited

U.S. PATENT DOCUMENTS 5,799,830 A 9/1998 Carroll et al.
6,955,076 B1 10/2005 Widt et al.
(Continued)

FOREIGN PATENT DOCUMENTS

EP 3757538 A1 12/2020

OTHER PUBLICATIONS

International Search Report and Written Opinion of International Application No. PCT/EP2022/060143 mailed on Jun. 28, 2022, 9 pages.

(Continued)

*Primary Examiner* — Eric S. McCall
(74) *Attorney, Agent, or Firm* — Heslin Rothenberg Farley & Mesiti P.C.; Victor A. Cardona, Esq.

(57) ABSTRACT

The sealing arrangement includes a connecting device and one or more housing parts of a housing unit for enclosing of a component, typically an attachment component forming a head of the connecting device. The gas permeable end formed in such component can be isolated, so that the sealing arrangement is adapted for use in detecting a detectable gas in a hermetically sealed detection chamber. Thanks to a sealing structure configured at a passageway for the fastening of the connecting device, a housing unit is obtained with a tight radial contact around an intermediate portion of the connecting device. The device is fitted with a flexible hose end, preferably at a barbed nozzle forming the end at the opposite from the gas permeable end. With such (Continued)

arrangement, the hose mounting can be tested for its integrity.

16 Claims, 5 Drawing Sheets

(51) Int. Cl.
*G01M 3/22* (2006.01)
*G01N 33/00* (2006.01)

(56) References Cited

U.S. PATENT DOCUMENTS

| | | | |
|---|---|---|---|
| 8,448,498 B1* | 5/2013 | Kelley | G01M 3/329 |
| | | | 73/49.3 |
| 9,097,609 B1* | 8/2015 | Kelley | G01M 3/32 |
| 2016/0087112 A1* | 3/2016 | Blakemore | G01J 5/0018 |
| | | | 257/433 |
| 2021/0364381 A1* | 11/2021 | Tos | G01M 3/226 |
| 2022/0316977 A1* | 10/2022 | Tos | G01M 3/205 |

OTHER PUBLICATIONS

Extended Search Report of European Application No. 21169252.0 mailed on Aug. 10, 2021, 5 pages.

* cited by examiner

SEALING DEVICE AND METHOD FOR DETECTING A POSSIBLE GAS LEAK AT A FITTING CONNECTION FOR BIOPHARMACEUTICAL PRODUCT

CROSS REFERENCE TO RELATED APPLICATIONS

This application is a national stage filing under section 371 of International Application No. PCT/EP2022/060143, filed on Apr. 14, 2022, and published on Oct. 27, 2022 as WO 2022/223476 A1 which claims priority to European Patent Application No. 21169252.0, filed on Apr. 19, 2021. The entire disclosure of each application is hereby incorporated herein by reference.

FIELD OF THE INVENTION

The invention relates to the field of connecting devices and similar accessories used in bag assemblies, which are provided as sterile components suitable for circulation and/or supply of a biopharmaceutical fluid. More particularly, the invention relates to a sealing arrangement, for use in integrity testing a hose/tube connection involving a connecting device, such testing being generally performed by detecting a detectable gas in a hermetically sealed detection chamber.

The term "biopharmaceutical fluid" is understood to mean a product resulting from biotechnology (culture media, cell cultures, buffer solutions, artificial nutrition liquids, blood products and derivatives of blood products) or a pharmaceutical product or more generally a product intended for use in the medical field. Such a product is in liquid, paste, or possibly powder form. The invention also applies to other products subject to similar requirements concerning their packaging. Such products are typically of high added value and it is important to ensure integrity of packaging where such products are contained, particularly the absence of any contamination.

For storage and transport purposes, it is customary to place such biopharmaceutical fluids in bags having a wall made of plastic that is flexible, closed, and sterile. It is essential that such bags be fluid tight when they receive biopharmaceutical fluid prior to use or during use of the biopharmaceutical fluid, or at least have a satisfactory level of fluid tightness, so that their possible content is preserved from any deterioration originating externally to the bag, such as contamination. It is therefore necessary to be able to easily detect any loss of integrity of the bag before, during, or after use. Same requirements apply for connecting parts, especially connections at a fitting or connections in a group of fittings or provided in 2D or 3D bag manifolds.

BACKGROUND OF THE INVENTION

Bag assemblies for a biopharmaceutical fluid comprise different components like hoses, adapters, fittings or connectors, reducers and filters. Such assemblies are vulnerable to leaks not only around seams and ports but also around the tube/hose connections, especially at hose barbs of components. An integrity testing of bag assemblies, using helium or similar tracer gas, can generally guarantee the leak tightness of all connections. This is of interest for eliminating the risk of filling a defective single use bag (else, a biopharmaceutical content of high value may be altered and/or lost, made unusable).

Leak testing a biopharmaceutical system before use typically requires forming a chamber wherein the system is placed in a test chamber, following which a differential pressure is established between the interior chamber delimited by the system (which may include hoses and one or more connectors) and the test chamber. A tracer gas is introduced to the higher pressure chamber and communication is established between the lower pressure chamber and a detecting apparatus such as a mass spectrometer which is sensitive to the tracer gas so as to detect any leakage of the tracer gas from the higher pressure chamber to the lower pressure chamber.

However, it is not always possible to observe if leaks are present between a connecting device and a conduit. For instance, many sterile connectors use a gas permeable membrane as sterile barrier, covering an open end of the connector at the opposite from the end provided with barb(s). The gas permeable barrier at the end of tubing lines poses a challenge for the integrity tests. Practically, the tubing must be clamped before the sterile connecting device, so that the connection of the hose around the hose-barb of a connecting device cannot be tested for its integrity and stays as a leakage or contamination risk in the assembly.

When a part of a system cannot be tested inside a vacuum chamber, a helium sniffing step can be performed manually. A leak may be possibly detected. However, manual sniffing operations and helium spraying as well are prone to operator variability when performing the leak test. They present higher dispersion in measurement and, accordingly, decrease sensitivity of the test method. Besides, it is often impossible to do such kind of test for complex products.

There is therefore a need, in particular in the specific field of the invention, for efficiently testing biopharmaceutical systems at fittings or connecting devices, such systems being intended to be filled with biopharmaceutical fluid, while detecting micrometric and possibly sub-micrometric holes as small as possible when testing the integrity of such connecting device before its use, simply and reliability, and typically with a level of reliability higher than with manual methods currently known or used.

OBJECTS AND SUMMARY OF THE INVENTION

For improving situation, embodiments of the invention provide a sealing arrangement, comprising:
- a housing unit provided with a first housing part, a second housing part and an access passageway, the first housing part and the second housing part delimiting an inner volume of the housing unit in a closed state, the inner volume being accessible via the access passageway;
- a connecting device, which comprises a tubular part extending from a first annular part to a second annular part, the tubular part delimiting a fluid passage and having an intermediate portion of annular shape arranged around the fluid passage, between the first annular part and the second annular part; and
- a sealing structure adapted to form a gas-tight junction at the access passageway, by a continuous contact around the intermediate portion, when the second annular part is received in the inner volume in the closed state of the housing unit;

wherein the first annular part is configured to be overlapped by a flexible hose end, while the second annular part is provided with an attachment component,
and wherein the housing unit is configured to receive the attachment component in the inner volume, so that at least one gas permeable end included in the attachment component is enclosed in the inner volume and gas escaping from the fluid passage via the at least one gas permeable end is kept in the inner volume.

Such solution is typically for use in detecting a detectable gas in a hermetically sealed detection chamber, in order to test integrity of hose connection around the first annular part of the connecting device, which may be a barbed nozzle. With such arrangement, detectable gas (tracer gas such as helium) used in the integrity test and flowing through the permeable end can be hermetically kept in the inner volume (not escaping outside the housing unit, until the housing unit is open), thus allowing the integrity test to be efficient.

Here, in the instant application, "hermetically" is used in its usual understanding in the field of leak detection, i.e. air tight, with a gas barrier effect. When a tracer gas is helium, a small part of this gas (which is very light) can possibly escape at low rate from an air-tight enclosure/housing unit, without impairing the integrity test. Accordingly, "hermetically" does not necessarily means "permanently helium tight": in contrast, such escape may occur at low rate (typically over a long period), without causing any difficulty for the purpose of detecting small leaks in the system under test.

The sealing arrangement advantageously provides a device to enable assemblies to get completely integrity testable with open/sterile end connectors at the end of their tubing. The housing unit may be a re-usable. The sealing structure may be at least partly re-used, possibly for a limited number of different tests. Thanks to the sealing structure, acting as a peripheral seal and configured at a passageway for the fastening of the connecting device, a housing unit is obtained with a tight radial contact around the intermediate portion of the connecting device.

The housing unit may be made of simple shells easy to be interlocked and preferably clamped. Such shells are designed in a manner that they can enclose air-tight the free end of a component like a connector at an end away/opposite from the hose barb or similar male part for connection to a hose.

Such kind of solution is of interest to implement a tracer gas test easily. As the connecting device typically is coupled to the hose, the sealing arrangement is of interest, in order to:
  in a preparation phase, forming a fluid transfer assembly, with the flexible hose end overlapping a barbed nozzle or similar first part of the connecting device and being optionally surrounded by a clamping collar; closing the housing unit by applying the sealing structure at interface between the housing parts and between the housing parts and the intermediate portion of the connecting device;
  in a test phase (using a detection chamber), allow injection of a tracer gas in an interior space including the fluid passage and the inner volume and separated/ isolated from the outside thanks to the sealing contact area between the housing parts completed by the sealing structure, and detecting any escape from the tracer gas toward a detection space of the detection chamber (due to a possible defect) by a tracer gas sensor device in fluid communication with the detection space.

The tracer gas, for instance helium, which is injected in the fluid passage can flow in the additional volume inside the housing unit. Such additional volume can be less than 25 or 30 $cm^3$, possibly less than 10 or 15 $cm^3$.

In the closed state of the housing unit, the sealing structure sandwiches the intermediate portion, using two distinct sealing means that form a sealing ring or similar annular part around the intermediate portion. Optionally, the sealing structure consists in two sealing members each delimiting a perimeter. This perimeter may match with shape and size of:
  a perimeter of a first joining edge included in the first housing part,
  a perimeter of a second joining edge included in the second housing part.

A groove (around the inner volume) may be formed, in the using unit, when joining the first joining edge and the second joining edge together. The sealing structure may extend in such interface groove.

More generally, the sealing means forming the sealing structure are adapted to tighten and seal around a neck or similar suitable section of the connecting device, in the intermediate portion. Typically, the second annular part is enclosed without any contact with the internal face(s) of the housing unit. More generally, it is understood that fastening and unfastening of the shells or analogous housing parts are simple operations, without any risk of degrading the first and second annular parts involved in connections.

In embodiments, the sealing arrangement may comprise at least two shells and at least two sealing means. The shells are housing parts designed in a manner that they can enclose gas-tight (hermetically) the free end of the connecting device involved in forming a fluid connection at the end of a flexible hose/tube. The sealing means may be distributed in two halves, each removably attached to one of the two shells. With the sealing means, helium diffusion is sufficiently retained or prevented, so that measures for leak test outside the housing unit (in a detection chamber for instance) are allowed efficiently.

More generally, the sealing structure is forming the gastight junction, in an integrity test configuration. The gastight junction prevents air around the housing unit from entering inside the inner volume and typically prevents any gas supplied via the fluid passage and reaching the inner volume from escaping from the inner volume.

The connecting device typically comprises a single piece that includes the first annular part and the fluid passage. The connecting device may be a single plastic piece. The housing unit may be made of two shells, preferably two halves that may be identical pieces in some options. With such construction, the preparation phase of the test is simplified.

In some options, the housing unit may be part of a multi cavity assembly that is configures to delimit several inner volumes, each associated with a passage way and suitable for enclosing a permeable end of a connecting device involved in forming a fluid connection at the opposite from the first annular part. The permeable end may be provided with a membrane that is preferably folded.

The first annular part of the fitting member may be provided with a retaining part including at least one retaining external annular rim or rib, adapted for locally deforming or increasing deformation of the flexible hose. Typically, the intermediate portion of the connecting device remains away from the flexible hose. The flexible hose in engaged state is provided with a contact part or tapering part sandwiched between an outer collar (which may be a clamping or crimping collar) and the retaining part.

Typically, the first annular part has a rigid connecting end forming a male tubular end suitable for insertion into an open connection end of the flexible hose forming a female part. Only the hose is deformed, while the nozzle-like part or insertion tubular portion of the second connector is not deformed.

In various embodiments of the sealing arrangement, one and/or the other of the following particulars may possibly also be employed, separately or in combination:

fluid communication between the inner volume and outside of the housing unit is only possible via the fluid passage, in the closed state of the housing unit.

one amongst the first housing part and the second housing part is attached (fixedly or removably) to a wall delimiting the detecting chamber and belonging to an integrity test apparatus.

the connecting device is a single-use device (disposable, since it cannot be re-used after a single-use with a specific biopharmaceutical fluid flowing through the fluid passage).

the first annular part is a barbed nozzle made of plastic;

the first annular part is provided with at least one relief, the first annular part preferably including at least one barb.

the first annular part is rigid and provided with a tapering part tapering away from the intermediate portion;

the first annular part is of smaller cross section than the second annular part;

the least one relief in the first annular part comprises an outer relief, preferably adjacent or close to an axial opening of the connecting device.

the first annular part is included in same plastic piece that includes the second annular part.

the plastic piece is a rigid piece of thermoplastic material.

the sealing structure comprises at least one piece that is sandwiched between a first rigid piece forming all or part of the first housing part and a second rigid piece forming all or part of the second housing part.

the sealing structure is located at a junction between the first housing part and the second housing part.

the sealing structure is resiliently deformable.

the sealing arrangement further comprises clamping members arranged at a periphery of the housing unit.

the clamping members are adapted for maintaining a compressed state of the sealing structure, by locking the closed state of the housing unit.

the clamping members may be arranged around the inner volume.

the two rigid pieces can be clamped together, in order to compress the sealing structure that is made of deformable plastic material.

the sealing structure comprises two deformable pieces each made of resilient plastic material.

the two deformable pieces of the sealing structure comprise two substantially planar parts (flat parts), parallel and joined to each other in the closed state, and a ring that is complementary to the two substantially planar parts.

the ring surrounds and encloses the intermediate portion.

the sealing structure is provided with a ring distributed in the two deformable pieces.

The connecting device may be a connecting piece adapted for sterile connection at the attachment component that forms a head part of the connecting device. The connecting device is provided with an annular recess or a neck, the intermediate portion extending at such annular recess or neck.

The connecting device may extend linearly, with the two opposite opening centered around same longitudinal axis.

In some embodiments, the at least one gas permeable end included in the attachment component comprises an end opening that:

belongs to the second annular part; and is covered by a gas permeable membrane.

Optionally:

the recess may form a groove provided with a bottom line of annular shape, preferably circular.

the bottom line of the groove is covered by the ring of the sealing structure.

the first housing part and the second housing part are made of or include metallic material.

the two housing parts are two pieces.

the metallic material may optionally be stainless steel.

one or more rigid clamping members, which may optionally extend in parallel bores (extending perpendicular to planar parts of the sealing structure), are used to close the housing unit and maintain/lock the housing unit in a closed state.

In various embodiments, the sealing structure may be provided with at least one of the following features:

the sealing structure is easily detachable from the connecting device.

the sealing structure surrounds the intermediate portion by extending in the annular recess of the connecting device.

the sealing structure has two superimposed sealing members, each provided with a bridge portion (rounded portion, preferably continuously curved).

the pieces of the sealing structure are preferably of same plastic material.

Optionally, the housing unit is provided with a connector fitting, preferably including metal, the connector fitting delimiting a communication channel that opens in the inner volume of the housing unit, outside the fluid passage.

The connector fitting may be included in/integrally formed with a single piece housing part (typically forming the first or the second housing part).

The connector fitting may include a non-return valve.

The housing unit may include a first connector fitting for suction and a second connector fitting for injection of gas, the second connector being used after stopping using the first connector.

According to another aspect, there is a need for an apparatus suitable for an integrity test, with ability to test a connection adjacent to an attachment component that has one or more gas permeable end(s). For this, it is provided an apparatus for use in detecting a detectable gas in a hermetically sealed detection chamber, the apparatus comprising the sealing arrangement according to the invention for positioning in a detection chamber.

This apparatus typically comprises:

a sterilized container for positioning in the detection chamber, this container having a flexible body at least partially defining an interior chamber for receiving and holding the detectable gas in the absence of a leak;

the sealing arrangement arranged with the fluid passage of the connecting device selectively communicating with the inner volume of the housing unit and with the interior chamber;

a hose including the flexible hose end connected to the first annular part of the connecting device and allowing fluid communication between the at least one gas permeable end and the interior chamber; and a sensor device associated with the detection chamber and capable of sensing the detectable gas external to the interior chamber, in a detection space of the detection chamber, as the result of the leak.

The housing unit and the sealing structure hermetically separate the inner volume, in which the attachment component having the at least one gas permeable end is received, from the detection space.

With such arrangement, the apparatus is appropriate for tightly separating, from the detection space, an interior chamber that is a tracer gas accumulating chamber.

The apparatus may also comprise a pumping assembly for creating a pressure differential between the interior chamber (detectable gas accumulating chamber) and the detection chamber.

In some embodiments, the apparatus further comprises a source of detectable gas and a valve associated to the source of detectable gas. The connecting device and the flexible hose end are connected at a coupling region for forming a fluid transfer assembly. The interior chamber is configured to be filled in the detectable gas when the valve is in an open state, via an injection line that communicates with the fluid passage via the interior chamber.

Optionally, a clamping collar is provided around the coupling region, such collar being configured to be permanently deformably crimped around a location of overlap between the flexible hose end and a shank part of the first annular part that is barbed. The shank part may typically extend between a shoulder or abutment portion (included in the connecting device) and a barb of the first annular part.

Besides, embodiments of the invention provide a method of leakage monitoring a fluid transfer assembly for fluid communication between two fluid receiving parts, in particular a fluid transfer assembly for use in a biopharmaceutical assembly, by using the sealing arrangement according to the invention, the method comprising, in a preparation phase:
  coupling the connecting device, which forms a first one of the two fluid receiving parts, to a hose to obtain a coupled state of the fluid transfer assembly, the coupling comprising inserting the first annular part as a male part inside the hose at a flexible hose end formed as a female part, the hose forming all or part of the second one of the two fluid receiving parts;
  delimiting an annular contact area at a coupling region where the flexible hose end overlaps on the first annular part;
  assembling the sealing arrangement so that the fluid passage selectively communicates with the internal volume of the housing unit;
and then in a test phase:
  injecting a tracer gas inside an accumulating space separated from a detection space by the annular contact area, in order to accumulate the tracer gas in the fluid passage, the detection space being located inside a hermetically sealed detection chamber;
whereby any escape from the tracer gas through a possible defect of the annular contact area can be detected in the detection space, by a tracer gas sensor device that is in fluid communication with the detection space.

Typically, the test phase is suitable for determining whether or not the annular contact area hermetically separates the detection space from the accumulating space.

In some embodiments, the tracer gas is fed via an injection line connected to a flexible bag or pouch delimiting. In variants, one amongst the housing parts includes a connector for gas-tight connection with a tracer gas injection line.

Vacuum suction may be performed inside at least one of the two fluid receiving parts, preferably in the two fluid receiving parts, a channel being used for vacuum pumping an amount of air present inside the connecting device.

Optionally, a detection step performed by the sensor device associated to the detection space may involve measuring information representative of the partial pressure of tracer gas, for instance helium, in the detection space. A mass spectrometer associated to a vacuum pump may be used for such vacuum pumping. If presence of tracer gas is not detected or partial pressure of such tracer gas not considered as reflecting a leakage situation, the annular contact is forming a sealing contact area passing the test, which may be a 2 μm test or any similar test for detecting any defect (for example with ability to detect defect size below 10 μm).

Then, in a subsequent step, the method may comprise comparing a test result representative of a tracer gas partial pressure drop in the detection space, which is obtained using the sensor device, to at least one reference result, in order to determine if the connection of the fluid transfer assembly is considered to have or not to have passed the test/integrity verification. Such step may be automatized for increasing test rate.

A flexible plastic bag may constitute or is a part of a bag arrangement including the flexible hose, each bag being suitable to receive biopharmaceutical product. The test is performed before any filling step for filling such biopharmaceutical product.

With such method, sensitivity may be good, and all the steps of the test phase can be performed in a same measuring cycle (for instance without modifying suction performed by at least one vacuum pump).

In various embodiments, one and/or the other of the following features may possibly also be employed, separately or in combination:
  a port of the flexible bag connects a flexible bag (connected to the hose) to a pressurization system including the gas tracer supplying device (gas source), using a feeding pipe or similar injection line.
  a pressure controlling device works as a control unit for emptying gas from the interior volume and optionally from a bag (connected to the hose).
  the pressure controlling device is configured to have the following steps performed successively: emptying the bag/injecting a tracer gas inside the connecting device and the housing unit, in an accumulating space/measuring the leak rate of gas tracer or any suitable parameter representative of the trace gas leakage.
  a valve arrangement is provided, which comprises at least one valve disposed between a source of pressurized helium or similar trace gas and a supplying line.
  the valve arrangement comprises at least one valve disposed between a vacuum pump and the accumulating space.

In various embodiments, one or more of the following may possibly be used, separately or in combination:
  each bag or at least one bag of an assembly including the connecting device has an outer envelope/wall delimiting a single internal space of the bag;
  the outer wall of the bag comprises a port suitable for being closed or connected in a fluid tight and removable manner to a mass spectrometer, possibly via a pipe;
  the bag is provided with a fill and/or discharge tube, which is located outside the outer envelope/wall.

the bag may include one or more connectors, filters, sensors.

BRIEF DESCRIPTION OF THE DRAWINGS

The figures of the drawings are now briefly described.

MORE DETAILED DESCRIPTION

A detailed description of several embodiments of the invention is provided below, accompanied with examples and with reference to the drawings.

In the various figures, the same references are used to designate identical or similar elements. Some size or thickness may be exaggerated for the purpose of better illustration.

The embodiments described provide examples and should not be interpreted as limiting the scope of the invention. Features from one embodiment or aspect may be combined with features from any other embodiment or aspect in any appropriate combination. For example, any individual or collective features of method aspects or embodiments may be applied to apparatus, product or component aspects or embodiments and vice versa.

Figure 1:
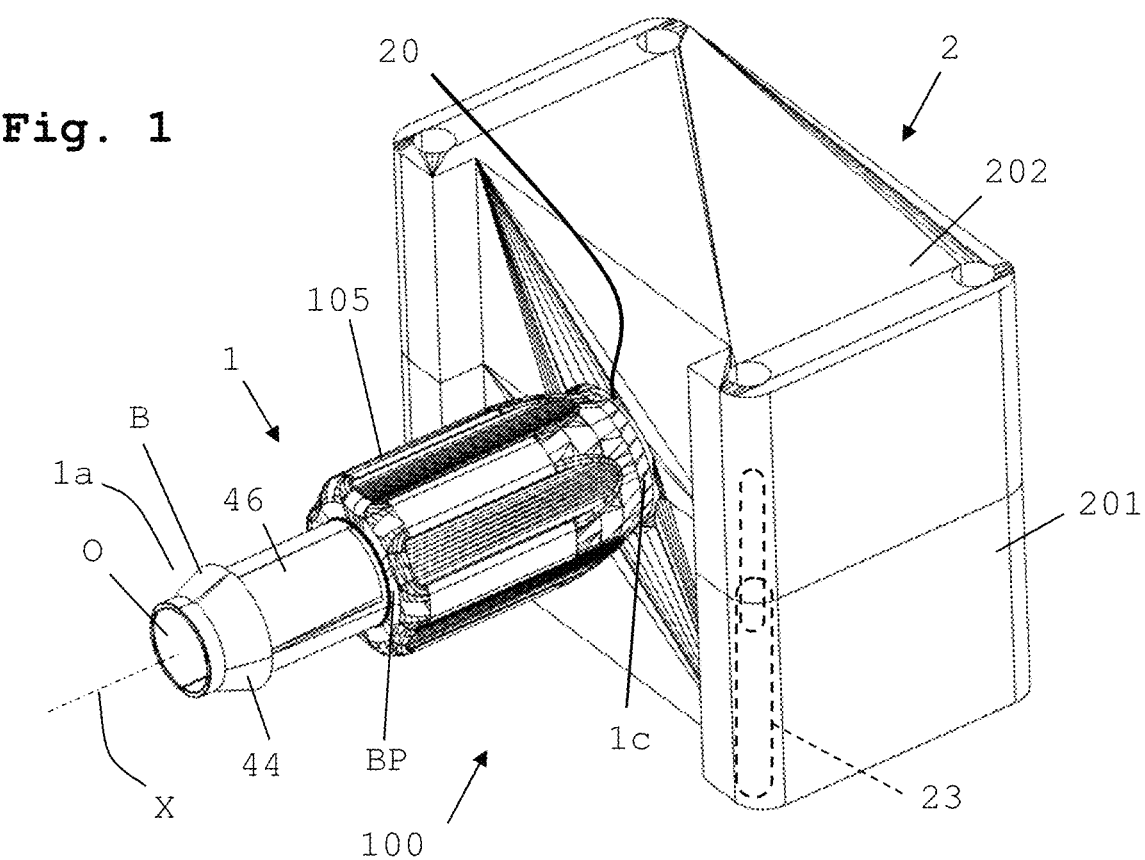
FIG. 1 is a perspective view of a sealing arrangement in accordance with an embodiment, in a configuration without any hose connected yet.
Figure 2A:
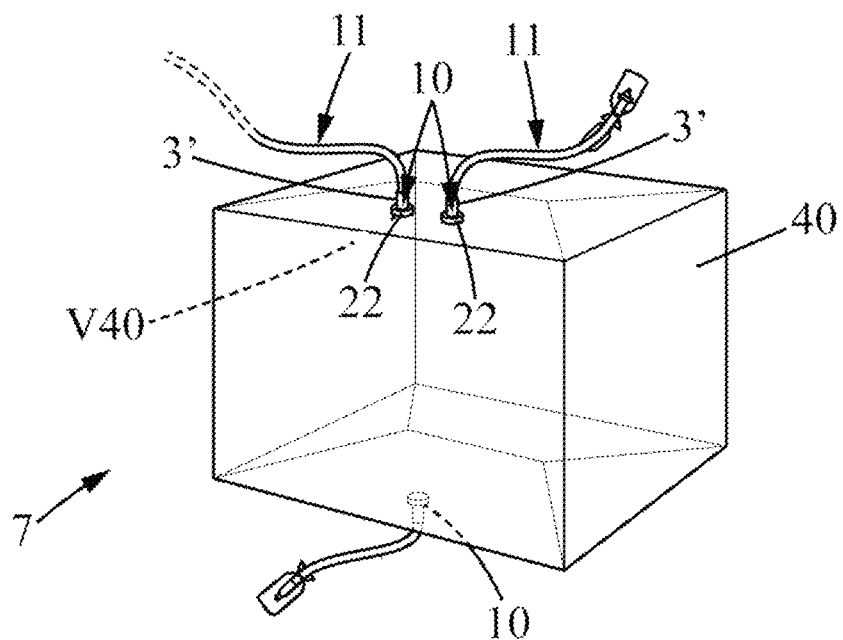
FIG. 2A is a view of a biopharmaceutical assembly provided with several flexible hoses, one of which possibly forming the conduit or hose for connection to the barbed nozzle of the connecting device shown in FIG. 1.
Figure 2B:
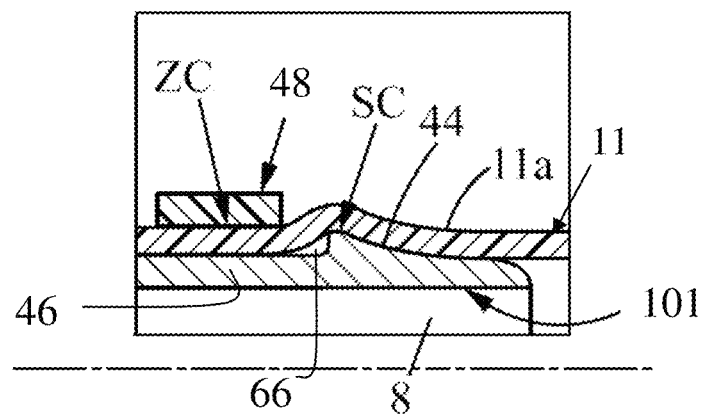
FIG. 2B is a detail in a longitudinal cut view of a fluid transfer assembly obtained at a first annular part of the connecting device that belongs to the sealing arrangement of FIG. 1.
Figure 6:
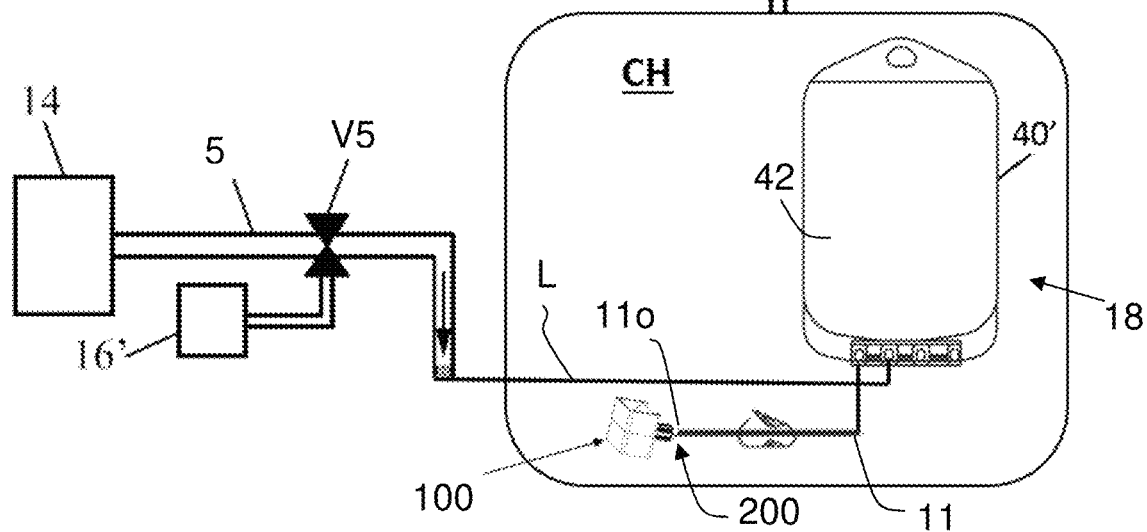
FIG. 6 schematically shows an embodiment of a testing system for verifying the integrity of a flexible container/pouch and one or more associated connections, including a connection between the connecting device of the sealing arrangement of FIG. 1 and a hose coupled to a flexible container/pouch.

FIGS. 1 and 2B show a connecting device 1 that is provided with a barbed nozzle 1a or similar male part suitable for fitting a hose end 11a of a hose 11 (flexible tube or the like). Such insertion end or male part is configured for insertion into a distal flexible hose end 11, such that the hose 11 extends over the one or more barb(s) B. As illustrated in FIG. 2A, such hose 11 may be coupled to a flexible container generally called pouch, for instance a 3D-pouch 40 or a 2D-pouch 40'. While a 2D-pouch 40' (such as illustrated in FIG. 6) remains relatively flat in filled state, since its peripheral seal remains planar, a 3D-pouch 40 has a parallelepiped volume when filled with the fluid, such pouch 40 having gussets.

Figure 3:
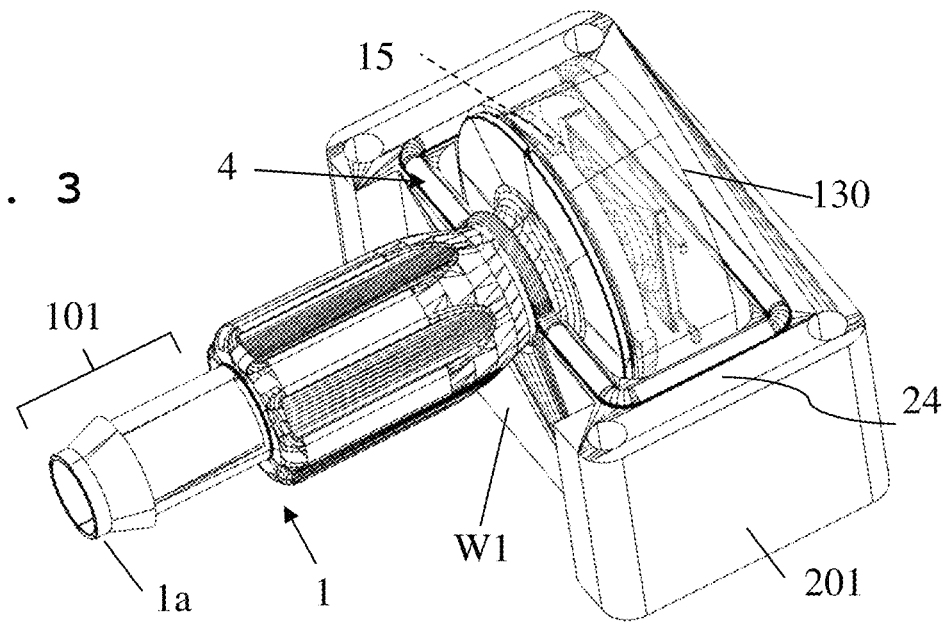
FIG. 3 is a view like FIG. 1, but with a housing part of the housing unit removed, so that an attachment component of the connecting device is apparent.
Figure 8:
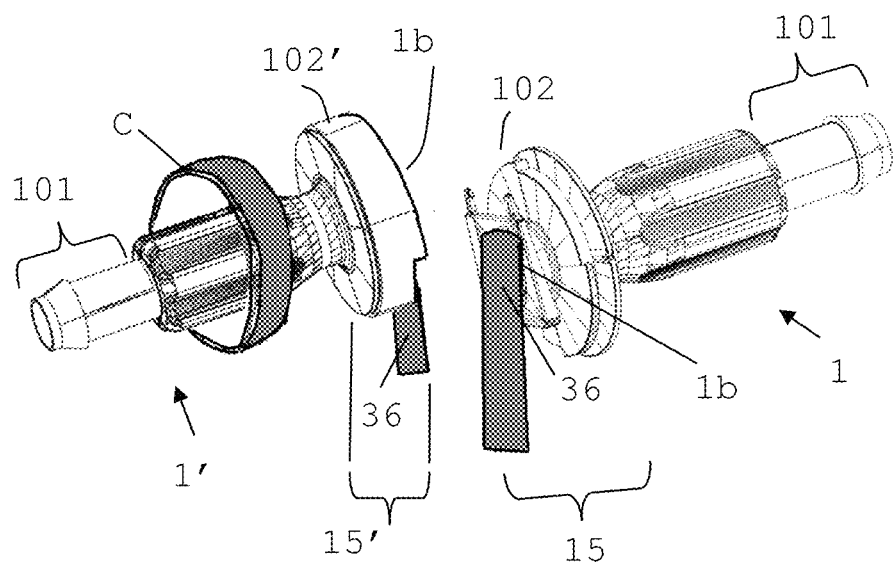
FIG. 8 shows an exemplary pair of connecting devices that can cooperate, in order to obtain a sterile connection for a biopharmaceutical fluid, the membranes being here adapted to be removed after a preliminary interlocking.

Referring to FIGS. 1, 3 and 8, the connecting device 1 or 1' may be a single tubular piece extending around a longitudinal axis X. The connecting device 1, 1' here comprises a tubular part extending from a first annular part 101 to a second annular part 102 or 102'. Such second annular part 102, 102' is intended to be attached to a complementary part after the hose 11 has been tightly connected to the first annular part 101. A gas permeable end 1b of the connecting device 1 is included in an attachment component 15 or 15' of the connecting device 1, 1', provided at the second annular part 102, 102'.

Figure 5:
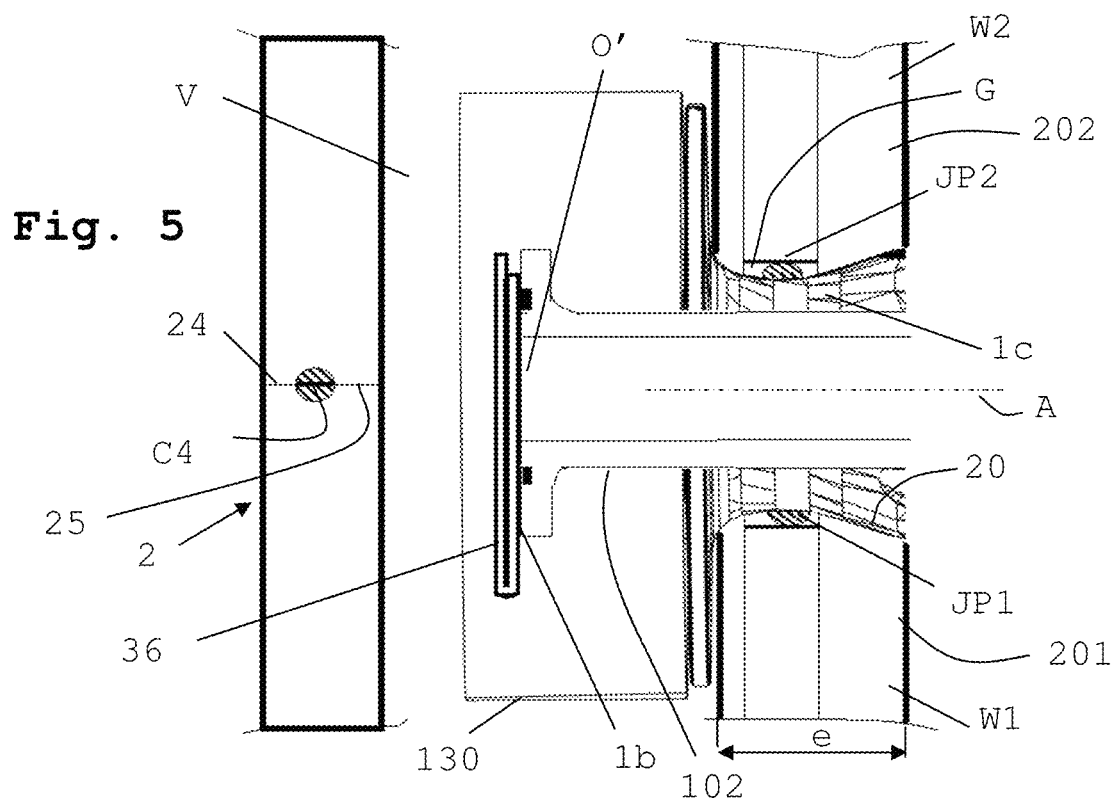
FIG. 5 is a schematic cut view of inside the housing unit, with illustration of the sealing structure sandwiched between the housing parts.

To allow the hose connection at the first annular part 101 to be integrity tested, the second annular part 102 may be received in an inner volume V delimited by a housing unit 2. Referring to FIGS. 1 and 5, the housing unit 2 may be a casing made of at least two housing parts 201, 202. The first housing part 201 and the second housing part 202 may be assembled by forming a peripheral seal at junction between two complementary joining edges 24, 25 of the respective housing parts 201 and 202.

The housing unit 2 may be provided with two wall parts W1, W2, here of same wall, which delimit a passageway 20 provided for passing an intermediate portion 1c of the connecting device 1, 1' through the wall of the housing unit 2. Typically, the housing parts 201, 202 may be hollow, forming two complementary shells. The wall with the access passageway 20 may be distributed in the two shells. In the non-limiting illustrated embodiments, such configuration with hollow housing parts 201, 202 is suitable for enclosing an attachment component 15, 15' that has an outer diameter significantly greater than the intermediate portion 1c and the first annular part 101. In some variants, only one of the housing parts 201, 202 is hollow and delimits the inner volume V.

Referring to FIGS. 1, 5 and 6, the connecting device 1 and the housing unit 2 cooperate together, with only the first annular part 101 available outside the housing unit 2, the second annular part 102 extending entirely in the inner volume V, beyond the access passageway 20 or similar opening. Here the connecting device 1 is fixed in relation to the housing unit 2, due to a clamping action around the intermediate portion 1c that extends through the access passageway 20. An assembled configuration is obtained, as illustrated in FIG. 1, with the housing unit 2 in a closed state. There is no leak passage between the intermediate portion 1c and the wall (W1, W2) delimiting the access passageway 20 because the intermediate portion 1c is maintained in gas-tight connection with a sealing structure 4 that is mounted between the housing parts 201, 202 (forming all or part of the peripheral seal).

Figure 4:
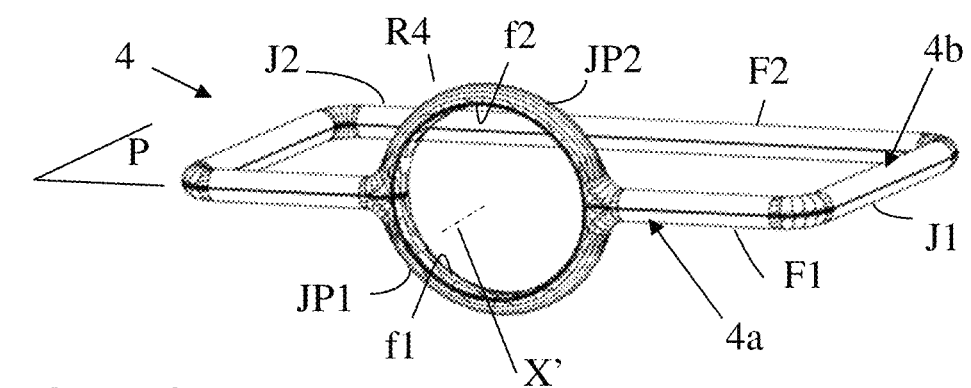
FIG. 4 is a perspective view of an exemplary sealing structure used in the embodiments of FIGS. 1 and 3.

As illustrated in FIGS. 4 and 5, the sealing structure 4 may have two separate sections JP1, JP2 forming an inner contact rim of annular shape, so that a continuous annular ring R4 is provided at the access passageway 20 in the assembled configuration. Here, a ring R4 extending around a central axis X', coaxial with the tubular part of the connecting device 1, 1', may be included in the sealing structure 4, so that following radial contact regions are obtained thanks to the sealing structure 4, at the access passageway 20:

an outer region with sealing structure-housing unit contact (using here a lower face F1 of a first deformable piece/member 4*a* and an upper face F2 of a second deformable piece/member 4*b*); and an internal region with sealing structure-intermediate portion contact, using internal faces f1, f2 of the two separate sections JP1, JP2.

The internal faces f1, f2 are typically included in bridge portions forming the sections JP1, JP2. They are optionally formed as symmetrical bridge portions (in a mirror inverted arrangement). Of course, the sealing structure 4 may vary in geometry (size, shape), depending on the intermediate portion 1*c* that surrounds the fluid passage 8 of the connecting device 1, 1', and of the particular geometry (size, shape) of the housing unit 2.

With such sealing arrangement 100, during an integrity test allowing the hose connection illustrated in FIGS. 2B and 6 to be tested in a detection chamber CH, gas circulating in the connecting device 1 via the opening O and escaping from the fluid passage 8 via the gas permeable end 1*b* is hermetically kept in the inner volume V of the housing unit 2 (no escape toward the detection space of the detection chamber CH).

The passageway 20 for the fastening of the connecting device 1, 1', which is delimited by the housing unit 2, is sized and shaped for fastening the device 1, 1' at the intermediate portion 1*c* by opposite compressing forces. Such opposite compressing forces are converted in a radial compression thanks to the sealing structure interposed between the intermediate portion 1*c* and the walls W1, W2 of the housing unit that respectively push this sealing structure 4, according to opposite directions (directions perpendicular to the junction plane P that will be described in further detail below).

Exemplary Embodiments of the Connecting Device(s)

The illustrated connecting device 1 extends linearly, with a connector/barbed nozzle forming the first annular part 101 for the hose 11 and an attachment component 15 for sterile connection with a corresponding attachment component 15' provided in the complementary connecting device 1'. Here, the housing unit 2 is adapted to cooperate with any one of the connecting devices 1, 1' shown in FIG. 8 since they have a same or similar intermediate portion 1*c* suitable for forming the sealing structure-intermediate portion contact, against the internal faces f1, f2.

The opposite end annular parts 101, 102 are here in alignment, but the present disclosure is not limited to use with straight/linear fittings or connecting devices and may also apply to other fitting members. For instance, elbow fittings or fittings that split or combine a flow of fluid therethrough may be provided. The lumen or fluid passage 8 may extend from a first opening O included in the first annular part 101 to a second opening O' included in the second annular part 102. More generally, it is understood that the connecting device 1, 1' may be provided with two opposite openings O, O', the second opening O' being possibly in a covered state when extending in the inner volume V of the housing unit 2.

In order to protect the second opening O', a cap 130 or similar rigid or relatively rigid plugging element may be provided. Referring to FIG. 3, the cap 130 may comprise a bottom and an annular skirt covering laterally all or part of the attachment component 15, 15'. Referring to FIG. 8, the cap 130 may directly cover an attachment component 15 or may cover a movable collar C that can be displaced relative to the attachment component 15'. Here such collar C may be a locker of the connection between the components 15, 15', surrounding at least one of these components 15, 15' in the coupled state of the sterile connection.

The tubular part delimiting the fluid passage 8 may be a single piece made of molded plastic material. Such material is not compressible in the intermediate portion 1*c*. A part of the intermediate portion 1*c* is of enlarged cross section as compared to the cross section at the free end delimiting the opening O. A gripping region of the connecting device 1, 1' is here obtained in such enlarged cross section part.

Typically, the attachment component 15, 15' provided at the second annular part 102 is radially fastened, fixedly, to the central tube section of the second annular part 102. The free end of this central tube section defines the second opening O'. An end flange or an annular rim is provided around this opening O, to form a receiving surface to which a membrane 36 covering the opening O' is detachably adhered.

As the membrane 36 has no barrier effect for gas, especially for helium or similar tracer/detectable gas used in an integrity test, the corresponding end of the connecting device 1, 1', at the second tubular part 102, is a gas permeable end 1*b*. Each membrane 36 may be folded, unfolding may be performed when attaching two connecting devices 1 and 1' via their attachment component 15, 15'. The connecting devices 1, 1' may be of the kind having a male component (attachment component 15 as illustrated in FIG. 8) cooperating with the female component (attachment component 15' shown in FIG. 8), using a locking slider and clips or similar locking members.

The illustrated connecting devices 1, 1' are of the range Opta® SFT sterile connectors from the Applicant. The connecting devices 1, 1' may allow fast and reliable sterile connection and sterile fluid transfer between two separate, pre-sterilized process components in biopharmaceutical manufacturing operations. Each membrane 36 may be a sterilizing grade Polyethersulfone (PES) membrane. The couplings or attachment components 15, 15' involved in locking the connection are provided with foolproofing means, for instance requiring a sliding or similar guiding along a direction perpendicular to the longitudinal direction of the connecting devices 1, 1' at the coupling region, or requiring a rotation along the longitudinal axis X.

The membranes 36 may be configured to be coupled, for instance at a pulling end, thus allowing simultaneous removal of the two membranes, before locking the connection between the components 15, 15'.

Figure 7:
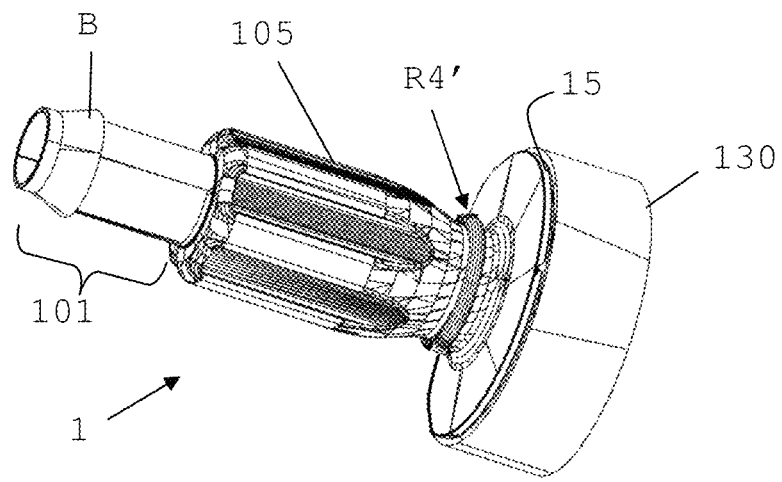
FIG. 7 illustrates a connecting device that may already supports a ring or any suitable annular member that for ensuring gas-tightness when in contact with the housing parts.

In the illustrated example of FIG. 1 or FIG. 7, a barb B is provided proximate to the opening O at an end of the fluid passage 8, here in a peripheral area adjacent to or delimiting the opening O of the connecting device 1. In some embodiments, more than one barb B may be formed adjacent to this opening O. The barb B may extend circumferentially around the fluid passage 8.

Referring to FIG. 2B, the barb B may provide a tapered surface 44 from a maximum diameter portion of the barb toward an insertion end. The insertion end corresponds with the opening O. The connecting device 1, 1' may optionally include a shoulder, a collar or similar abutment portion BP, in order to limit a magnitude of insertion of the insertion end into a corresponding conduit delimited by the hose 11. A shank part 46, which may be substantially cylindrical, is optionally defined as the portion of the connecting device 1 between the barb B and the shoulder formed by the abutment portion BP. The barbed nozzle 1*a* is here composed of the shank part 46 and the connector end part provided with the one or more barb(s) B.

The abutment BP can be a transition between the shank part 46 and a gripping portion 105, optionally provided with ribs, here longitudinal ribs.

The connection (fluid connection between the annular part 101 and the associated hose 11) shown in FIG. 2B can be a connection under test, once the other annular part 102 has been tightly fastened to the housing unit 2. It is thus obtained a fluid transfer assembly 200 (see also FIG. 8), suitable for flowing of a fluid from or to the interior volume of the hose 11, through the fluid passage 8. Tightness of this fluid connection can be controlled when the hose 11 is already connected to a bag 40 or 40', for instance in fluid communication with an interior volume V40 of the bag 40 illustrated in FIG. 2A or the pouch 40' illustrated in FIG. 6.

Exemplary Construction of a Bag Assembly

The assembly 7 of FIG. 2A shows that a hose 11 may be suitable for transferring fluid (when coupled to a connecting device 1, 1') inside a fluid transfer circuit and/or for forming a connection on at least one supply or transfer port 22 of a container such as flexible bag 40. The flexible bag 40, which can contain large biopharmaceutical fluid capacity, may form a receiving volume of the biopharmaceutical fluid transferred via a connection. A fluidic connection device 10 can be included in the container 40 and may be provided for any suitable fluid transfer application, in a manufacturing step of the biopharmaceutical industry, in one or more stages of research and development, of quality control, for conveying a fluid to a filtration stage, without these examples being limiting. The same applies for the hose 11 connected to the barbed nozzle 1a of the fluidic connecting device 1, 1'.

The bag 40 is here in the form of a flexible bag which can be initially folded to be flat. It can be defined generally as a flexible enclosure essentially delimited by a set of walls. One of the container walls (receiving wall) can integrate at least one port connector assembly. The same applies for the pouch 40' shown in FIG. 6. More generally, the set of walls or "receiving wall" forming the container 40, 40' delimits a fluid space V40 in communication with the circulation volume of the hose and the connecting device 1, 1', thus in communication with the fluid passage 8.

Referring to FIG. 2B, it is understood that a coupling region, corresponding to location at which the flexible hose end 11a is overlapping on the barbed nozzle 1a or similar annular part 101, is obtained. The corresponding open end 110 (FIG. 6) of the hose 11 thus may extend beyond the area of higher radial deformation of the flexible hose end 11a, where one or more annular sealing contact area(s) SC are provided between a tubular external surface of the annular part 101 (here delimited by the barb B) and an interior surface of the flexible hose end 11a.

The barbed nozzle 1a is suitable for connecting, via the flexible hose end 11a, the connecting device 1, 1' and a container or bag 40, 40' of biopharmaceutical product. A fluidic connection device 10 is provided for assembling such flexible hose 11 to a connector of a transfer port 22, which is provided in the container or bag 40, 40'. Here, the transfer port 22 may be connected to an end of the flexible hose 11 opposite to the flexible hose end 11a that overlaps the barbed nozzle 1a. As the flexible hose end 11a is surrounding the barbed part forming the nozzle 1a, tight connection is usually obtained, except in case of defects. A tracer gas test is of interest to prevent using a connection that is not sufficiently tight, i.e. a connection where a defect of size of about 2 μm or more can be detected.

In view of the assembly 7 of FIG. 2A, it is understood that one or more connecting devices 1, 1' can be used for obtaining a fluid transfer circuit, for instance by connection to a bag/container arrangement. A container arrangement comprising one or more flexible disposable bags 40, 40' may be assembled and then integrity tested. Each of the flexible disposable bags 40, 40' has an inlet element or port, to which a flexible connecting tube/hose is attached (with aseptic connection). An aseptic connector may be provided at this input end. Referring to FIG. 6, the container arrangement/assembly 18 may be provided with one or more clamps or clamping means for clamping a hose. A clamp, here made of a material more rigid than the materials of the other parts of the assembly 18, may be provided to selectively isolate a corresponding bag 40 or 40'.

More generally, the connecting device 1, 1' may be used in any kind of container arrangement 18 comprising one or a plurality of bags 40, 40' or arrangement with two complementary devices connected by the coupling between the connecting devices 1 and 1'.

Typically, the connecting device 1, 1' as illustrated in FIGS. 1 and 8 is separate from such container 40, 40'. The connecting device 1, 1' preferably belongs to a fluid transfer assembly 200 that is separate from any wall of a container/bag 40 or pouch 40'. When preparing an integrity test, the connecting device 1, 1' is already assembled in the sealing arrangement 100, so that the permeable end 1b is closed, by being enclosed in the inner volume V of the housing unit 2. The hose 11 is also connected to the first annular part 101 and allows communication with a tracer gas by being connected to a pouch/bag 40, 40' receiving such gas (injected via a suitable injection line L), or possibly by being directly connected to a tracer gas supplying part.

Referring to FIG. 6, in a preparation phase before the test phase of the integrity test, the bag assembly 18 is prepared, by connecting the hose end 11a to form the fluid transfer assembly 200. This bag assembly 18 is placed inside a testing apparatus, in a detection chamber CH thereof. The injection line L is adequately connected to the pouch 40' so that the injection line selectively supplies the tracer gas, for instance helium or argon, in the interior space delimited by the bag assembly 18 (including the fluid passage 8). Accordingly, a differential pressure is established between this interior space and the test chamber, hereafter called detection chamber CH. The housing unit 2 forms a gas-tight barrier between the interior space and the detection space of the detection chamber CH. The annular contact area SC (see FIG. 2B) at coupling region where the flexible hose end 11a overlaps the shank part 46, is thus also tested since any leak at such location would cause the tracer gas in the passage 8 to escape to the detection chamber CH.

The hose 11 may have an inner diameter selected for suitable use with the barbed nozzle based upon the size of the lumen or fluid passage 8 and the wall thickness of firs annular pat 101. The hose 11 may have an interior surface and a wall thickness selected for its suitability to withstand internal fluid pressures depending upon the use of the hose 11. The hose 11 may be a single-walled conduit. More generally, use of single-walled conduits may be preferred to minimize any interstitial space that could occur between the walls of multi-wall conduits, which could create opportunities for leaks or bacteria growth.

According to some embodiments, surface contact between the barb B and the hose 11 is considered sufficient for retention of the hose 11 on the annular part 101 of the connecting device 1, 1'. In other embodiments, fasteners, such as cable ties, ear clamps or similar clamping collars 48, are secured around the hose 11 along the region of the shank part 46, preferably selectively around the shank region.

The annular end rim of the hose 11 that belongs to the distal part is not surrounded by such clamping collar. As this annular end rim has been temporary deformed and enlarged, it typically fails to ensure tight contact around the shank part 46. Referring to FIG. 2B, thanks to the clamping collar 48 (or other relatively rigid piece, or elastomeric sleeve or similar sleeve), the hose 11 may be secured to the barb B by creating a seal between the barb B and the interior surface to minimize or suppress gas leaks therebetween. In the coupling region, the flexible hose end 11 has a distal part around the shank part 46, which is less deformed (in the coupled state) than a proximal part surrounding the barb B to create such seal.

In options with a crimping collar 48 added around the hose end section, the crimping of this collar 48 in the shank part region may be performed after the annular contact area SC is obtained, in order to have the collar inner diameter decreased below the maximum outer diameter of the hose end (at the barb B). The additional contact area ZC between the crimping collar 48 or similar clamping ring is located/ extends longitudinally between the abutment portion BP and the barb B, here around a cylindrical shank part 46.

While the drawings show embodiments with a single clamping collar 48, in order to perform a reinforcement step, any suitable binding element, possibly a pair of binding elements, can be used to provide a clamping effect and ensure the hose 11 cannot be accidentally removed. In some variants, the collar 48 may be replaced by a single layer sleeve, a multilayer sleeve, or a combination of a sleeve or liner and a more rigid collar (for instance elastomeric sleeve or liner and a metallic sleeve/collar).

The fluid transfer assembly 200 may be obtained in various manners. Here, it is obtained once the insertion end 11*a* of the hose 11 overlaps the barbed nozzle 1*a*. The hose 11 may be inserted until all or part of the flexible hose end 11 abuts the abutment portion BP. Additionally or alternatively, the barbed nozzle may be inserted until the flexible hose end 11*a* reaches the passageway 20 or partly extends in the inner volume V.

Referring to FIG. 2B, the fluid passage 8 may have a longitudinal axis A that is a central axis of the second annular part 102. In the closed state, such axis A corresponds to a central axis of the passageway 20. Such axis may also correspond to the longitudinal axis X of the connecting device 1, 1'.

Mounting of the Sealing Structure on the Housing Unit

The housing parts 201, 202 are typically incompressible parts so that the housing unit 2 can compress the sealing structure 4. In a first embodiment, as illustrated in FIGS. 1 and 3-5, the junction between the housing parts 201, 201 mainly extends planar. In this embodiment, the first housing part 201 and the second housing part are identical pieces. The passageway 20 delimited by the housing parts 201, 202, here between two walls W1, W2, has an extension length corresponding to thickness e of the housing unit front wall that includes the two walls W1, W2. One or two slots in the housing parts 201, 202 may form the passageway 20. Two half-circle slots may be preferred to facilitate encircling of the intermediate portion 1*c*, without confusion in assembling operation.

The sealing structure 4, which is compressible, may extend in an interface groove G obtained by recessed sections in the thickness of the housing unit side walls, as shown in FIG. 5. Here, such interface groove is an interior groove so that the sealing structure is typically not seen from the outside in the closed state of the housing unit 2. In variants, the sealing structure 4 extends at junction between the housing parts 201, 202 and beyond external faces and/or beyond internal faces of the housing unit 2.

The sealing structure 4 may comprise or consist in two sealing members 4*a*, 4*b*, which are preferably two pieces. More generally, the sealing structure 4 comprises at least one piece that is sandwiched between:
- a first rigid piece forming all or part of the first housing part 201,
- and a second rigid piece forming all or part of the second housing part 202.

In the first embodiment, the two deformable sealing members 4*a*, 4*b*, which are each made of resilient plastic material, comprise:
- two substantially planar parts J1, J2, parallel and joined to each other in the closed state (with an interface contact C4, which is a direct contact between theses planar parts), and
- a ring R4 that is complementary to the two planar parts J1, J2.

The ring R4 typically surrounds and encloses the intermediate portion 1*c*.

Before closing the housing unit 2, the first sealing member 4*a* may be mounted in a lower groove part that belongs to the first housing part 201. Referring to FIGS. 3-5, the first sealing member 4*a* has a half ring part or similar curved part, forming a first one of the two separate sections JP1, JP2. Then, the connecting device 1 (or the device 1') is fastened to the first housing part 201 with a part of the intermediate portion 1*c* resting on the internal face f1. The intermediate portion 1*c* extends (provisionally) through the corresponding slot of the first housing part 201.

Optionally, such internal face f1 may extend below (entirely below here) a junction plane P for the junction between the sealing members 4*a*, 4*b*. This face f1 is typically half circular and/or adequately matches with shape and size of the contact region in the intermediate portion 1*c*. The internal face f1 is included in the first section JP1 that belongs to the first sealing member 4*a*. Such first section JP1 may be received in a groove part that is shifted downwardly as compared to the remainder of the interface groove G, due to the slot in the first housing part 201. Similarly, another groove part may be shifted upwardly as compared to the remainder of the interface groove G, due to the slot in the second housing part 202.

Once the intermediate portion 1*c* has been placed in contact with the first sealing member 4*a* and extends through the slot for having the attachment component located between the walls of the first housing part 201, the housing unit 2 can be closed by having the second sealing member 4*b* applied around the intermediate portion 1*c*, in order to complete the first sealing member 4*a*, thus forming the ring R4 around the corresponding section of the connecting device 1, at the intermediate portion 1*c*.

In order to form such ring R4 of the sealing structure without delicate handling of sealing members for the operator, each of the sealing members 4*a*, 4*b* may already be fastened to the corresponding housing part 201 or 202. Some interlocking reliefs and/or guides may be provided at the joining edges 24, 25 of the housing parts 201, 202.

In the closed state, the ring R4 may extend perpendicular to a junction plane P where the planar parts J1, J2 are in contact with each other; as illustrated in FIGS. 4-5.

The joining edges 24, 25 allow for a compression of the sealing structure 4, with the sealing members 4*a*, 4*b* possibly deforming along a radial direction (parallel to thickness direction of the housing unit side walls). Indeed, the housing parts 201, 201 are rigid and interspace height between the joining edges 24, 25 in the closed state may be inferior to nominal size/section height of the sealing structure. In the first embodiment, such interspace is obtained at the interface groove G, with the interspace height measured perpendicular to the longitudinal axis X of the connecting device 1 and typically perpendicular to the junction plane P.

The sealing structure 4 typically tightly surrounds the intermediate portion 1c, which extends through the front wall, in an intermediary region between a bottom wall and a top wall of the housing unit 2. In the closed state, the front wall (including the two walls W1, W2) extends from the bottom wall to the top wall, for instance perpendicularly to the bottom wall and top wall. In variants, the housing unit 2 has rounded geometry and/or comprises a top wall that is not parallel to the bottom wall.

A clamping may be performed, in order to lock the closed state of the housing unit 2 with the sealing structure 4 resiliently deformed at a peripheral seal. For instance, the sealing arrangement 100 is provided with clamping members 23 arranged at a periphery of the housing unit 2, around the inner volume V, for maintaining a compressed state of the sealing structure 4. The two rigid pieces forming the housing parts 201, 201 can be clamped together, in order to compress the sealing structure 4 (sandwiching with constraining effect to deform cross section of the sealing member(s) 4a, 4b). The clamping members 23 may be provided with screw(s) and/or bolt(s), one or more amongst tie rods, clamping levers or any suitable clamping assembly. These members allow for a removable connection. Indeed, after an integrity test, the housing unit is disassembled without any risk of altering the tested connection (just removing two shells with associated sealing members 4a, 4b).

In the first embodiment, the ring R4 is distributed in the members 4a, 4b and thus formed after the second annular part 102 is received in a housing part of the housing unit 2. In a second embodiment and in some variants, as illustrated in FIG. 7, the ring R4' can be a single piece and/or be attached around the intermediate portion 1c before assembling the housing unit 2 to obtain the sealing arrangement 100. In some options, such ring R4' may be shrinkable (as shrink-wrap material) to form a shrink-seal. Possibly, the sealing structure has a flat part distinct from the ring R4' and provided with contact ends that are also compressed to form a gas-tight contact against the ring R4'. Such flat part may already be fastened to at least one of the housing parts 201, 202, forming a peripheral seal that defines a partial or whole circumference.

More generally, it is understood that the ring R4; R4' or similar annular layer of deformable material that surrounds the intermediate portion 1c is complementary to the one or more parts, possibly two planar parts J1, J2, involved in sealing the interface between the joining edges 24, 25.

Besides, the cross-section of each sealing member 4a, 4b (which may be identical) may vary. Such cross-section may vary, being for instance flat or planar at least at the separate parts J1, J2 not in contact with the intermediate portion 1c. Also, the sealing structure 4 may have a section that is circular, oval, H-shaped (in this latter option, the sealing structure 4 may sandwich respective wall edges of the housing parts 201, 202).

Material Used in the Sealing Arrangement

The connecting device 1 may be a fitting piece formed from molding, casting, additive manufacturing, or other known processes. The connecting device 1 may be made from thermoplastics such as polyolefins, polypropylene, polyethylene, polyoxymethylene (POM), polyvinylidene-fluoride (PVDF), polytetrafluoroethylene (PTFE), polyamide, polysulfone, polyester, polycarbonate, and glass filled thermoplastics. The connecting device 1 may also be made from thermosets such as epoxies, pheonolics, silicone, copolymers of silicone and novolacs. Other suitable materials may include cyanate ester, polyurethanes, and urethane methacrylate.

The housing unit 2 may be made of any suitable rigid material, typically metallic material. The inner volume V may be delimited by inner faces made of stainless steel. The housing unit 2 may be hinged, for instance for guiding movement of a housing part 202 acting as a cover relative to the complementary housing part 201.

The sealing structure 4 is made of soft material, for instance Silicone or TPE. Such soft material is not porous (and typically not hollow) and suitable for having a gas-barrier effect. This sealing material may be compressed, so that thickness of the sealing structure may resiliently decrease, the sealing structure 4 being compressible preferably with at least 10% of thickness decrease.

The flexible hose 11 may preferably be a flexible conduit suitable for use in medical or pharmaceutical environments. The flexible hose 11 may be constructed of a thermoset or a thermoplastic polymer. If a thermoset is used, silicones, polyurethanes, fluoroelastomers or perfluoropolyethers are preferred construction materials for the conduits. If a thermoplastic is used, C-Flex® tubing, block copolymers of styrene-ethylene-butylene-styrene, PureWeld, PVC, polyolefins, or polyethylene are preferred construction materials. In some options, a flexible hose 11 constructed from ethyl-ene-vinyl acetate (EVA) may be preferred due to the ability to weld together components made from EVA.

The flexible hose 11 has here a circular cross-section and has a characteristic outer diameter and a nominal inner diameter. Such diameters are of constant size, so that the hose thickness may typically be constant. A hose thickness inferior or equal to 5 mm may be preferred, such thickness being typically not inferior to 0.5 mm (to have sufficient mechanical strength). Thickness may be in the range from 1.5 to 3.2 mm. The material of the hose may be translucent or transparent in some options. The material of the connecting device 1, 1' may be opaque.

Exemplary Use of a Sealing Arrangement in an Integrity Test

Referring to FIG. 6, it can be seen a way of performing a test regarding the connection of the fluid transfer assembly 200. After the preparation phase, the fluid transfer assembly 200 can be tested, alone or together with the bag assembly 18. When a bag or pouch 40, 40' is connected via the hose 11 to the connecting device 1, 1', a reinforcement step may be optionally performed during the preparation phase, for instant using a clamping collar (possibly a crimping collar 48). The connection may be finalized with or without a clamping collar 48. Using a collar 48 that clamps the part of the flexible hose end 11 surrounding the shank part 46 may be of interest to prevent any accidental removal of the flexible hose end 11a (such removal being due to fluid pressure). A clamping collar 48 may also help in limiting production of a leak point due to air gap 66, at rear of a barb as illustrated in FIG. 2B. But such effect may depend on the way it is installed/clamped/crimped.

The apparatus for the integrity test is an apparatus provided with a hermetically sealed detection chamber CH. The apparatus may be provided with a fixed main body or base of an enclosure. A seal member (not shown) is provided for the removable reception of a cover member, which may be a hollow cover member or a plate member. In fitted state using the seal member, the cover member and the main body form the detection chamber CH.

This apparatus is here suitable for:
injecting a detectable gas (tracer gas such as helium or argon) inside the detection chamber CH, more particularly in a bag assembly or analogous system under test; and
detecting this gas in the detection chamber CH in case of a leak.

Here the system under test is sterilized container 40, 40', which is positioned in the detection chamber CH. This container has a flexible body at least partially defining an interior chamber 42 for receiving and holding the detectable gas in the absence of a leak. Of course, the part to be tested can be any one of a large number of different devices, here provided with at least one sealing arrangement 100. Referring to FIG. 6, the apparatus comprises the sealing arrangement 100 for positioning in the detection chamber CH, the hose 11 including the flexible hose end 11o connected to the first annular part 101 and allowing fluid communication between the gas permeable end 1b and the interior chamber 42.

The apparatus has a pressurized tracer gas unit 14 or similar gas source, provided with an injection channel 5. A valve V5 located outside the detection chamber may be provided to control feeding of helium or similar tracer gas via the injection channel 5. Optionally, this channel 5 communicates with a hose acting as supplying line L and connected to the container forming the interior chamber 42. More generally, a tracer gas is supplied in an interior space of the system under test and flows through the fluid transfer assembly 200 to the gas permeable end 1b, such end 1b being arranged inside the housing unit 2 of the sealing arrangement 100. The tracer gas cannot escape via the housing unit 2, so that the connection with the hose end 11a can be tested. Indeed, the housing unit 2 and the sealing structure 4 hermetically separate the inner volume V from the detection space inside the detection chamber CH.

In some variants, the housing unit 2 may be provided with a connector suitable for connection to a tracer gas injection line. The specific connector of the housing unit may be included in one of the housing parts 201, 202. In such variant, the tracer gas circulates in the inner volume V before reaching the fluid passage 8. This option is less preferred when a pouch or bag 40, 40' is also tested, as tracer gas filling duration may increase.

Figure 9:
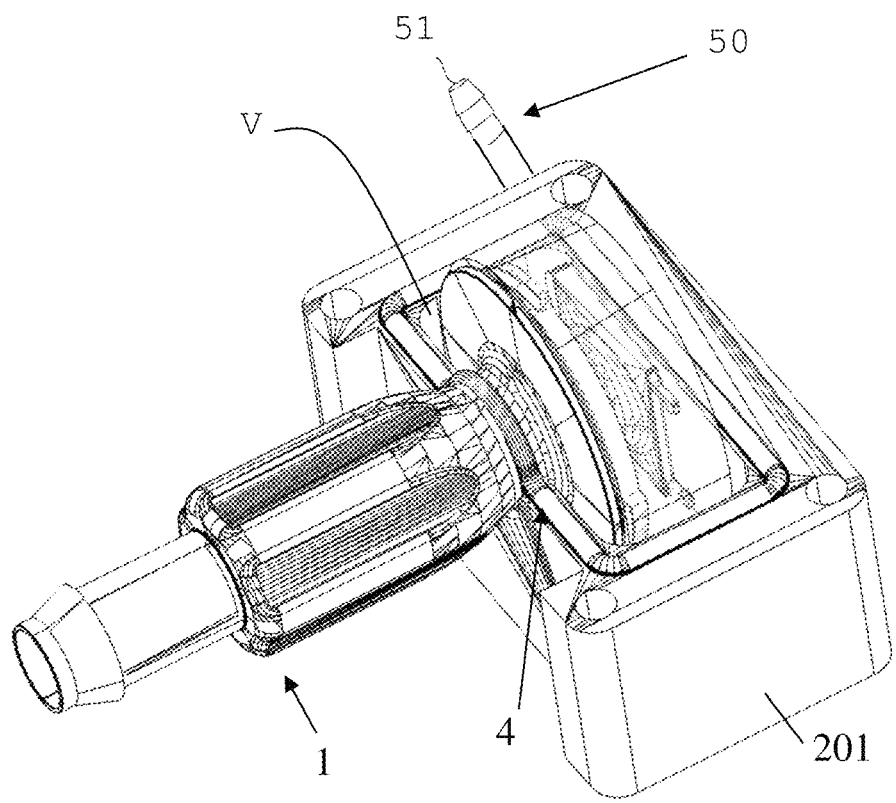
FIG. 9 is a view like FIG. 3, the housing part being here provided with a connector fitting protruding outwardly, such fitting allowing suction directly in the housing unit.

The communication channel 50 formed by the connector fitting 51 shown in the optional embodiment of FIG. 9 may be used for such connection to the tracer gas injection line and/or for allowing suction on the external side relative to the membrane 36. Such suction, directly in the inner volume V of the housing unit 2, may be a second suction combined with a first suction performed from the internal side of the membrane 36. This first suction may use a line associated to the vacuum pump 16', which possibly includes a part of the supply line L for tracer gas injection.

When suction is also performed directly in the housing unit 2, faster vacuum may be established. More generally, an access (input and/or output access) to the inner volume V at the housing unit 2 can be provided. When combined suction is established, gas diffusion through the membrane 36 (possibly depending of the kind of membrane) is not a limiting effect at the end of the suction for reaching high vacuum. It is understood that with an additional input/output access at the housing unit 2, evacuation of the inner volume V can be done separately through this connection.

Still referring to FIG. 6, the apparatus may comprise a pumping assembly for creating a pressure differential between the interior chamber 42 and the detection chamber CH. For instance, a vacuum pump 16' may be present to allow vacuum pumping, before performing tracer gas injection. Vacuum is obtained in the detection chamber CH. Two vacuum pumps may be present, for evacuating each amongst the interior chamber 42 and the detection space (around the system under test). Suction has to be performed, in order to decrease pressure in the chamber CH.

In options with the housing unit 2 having at least one connector fitting, a vacuum pump associated to the connector fitting 51 may also enable suction, in order to decrease pressure in the inner volume V. Such pump is optionally a vacuum pump separate from the other vacuum pump(s) 16'. In some constructions, such suction via the communication channel 50 is performed by a suction line connected to a vacuum source that is already available, for instance using a branching connected to same vacuum pump 16'.

The channel 5 may be optionally used for emptying the interior chamber 42 and obtain a vacuum or low-pressure state inside the system under test. FIG. 6 schematically illustrates an option to have such vacuum pump 16' connected to same channel 5. In a preparation phase before sensing the tracer gas, the vacuum pump 16' is selectively activated, while the tracer gas unit 14 is in OFF or similar inactivated state.

In connected state between a bag port and the supplying line/channel 5, the valve V5 may be actuated to selectively feed the tracer gas in the interior chamber 42, only after the barbed nozzle 1a has been inserted inside the flexible hose end 11a, thus after obtaining at least one annular contact area SC (annular contact for sealing the connection) such as shown in FIG. 2B. Such annular contact is typically a sealing contact between the tapered surface 44 and the interior surface of the flexible hose end 11a.

The apparatus also comprises a sensor device 9 associated with the detection chamber CH and capable of sensing the detectable gas external to the interior chamber 42, in a detection space of the detection chamber CH, as the result of the leak in the system under test. A port 30 or pipe, separate from the channel 5, is provided for connecting the sensor device 9 to the chamber CH. At least one valve may be used for controlling a suction associated to the port 30 communicating with the sensor device 9. For instance, a valve may allow selection between a vacuum pump distinct from the vacuum pump 16' and the tracer gas sensor device 9. In the testing apparatus, the one or more valves may be solenoid valves.

The sensor device 9 may be under the form of a mass spectrometer or similar detecting apparatus, which is sensitive to the tracer gas so as to detect any leakage of the tracer gas. Here, pressure may be lower in the detection chamber CH around the system under test (higher vacuum since no gas has been injected). Accordingly, the interior chamber 42 is the higher-pressure chamber, while the detection space around the system under test (here bag assembly 18) is the lower pressure chamber.

Thanks to adequate actuation of the valve 5, at the beginning of the test phase, a tracer gas is introduced to the higher-pressure chamber and communication is established between the detection space (lower pressure chamber) and the sensor device 9.

The monitoring phase (test phase) of the measuring cycle may be performed, after suction step(s) and tracer gas injection, using an analyzing module of a suitable control unit 13. At the beginning of the measuring cycle, the testing apparatus may be similar to known systems in that it is required to reach a low-pressure threshold, after a waiting period. Then, a pressure drop may be analyzed to conclude regarding integrity of the system under test.

Any suitable analysis module 19 may be configured to set a suitable partial pressure of tracer gas, which is representative of a leak. In some options, such analysis module may be associated to or included in the tracer gas sensor device 9 and can:
- use information representative of helium partial pressure detected for a period that includes a period subsequent to the injection step, typically when a suction mode is active; and
- compare the test result to at least one reference result, in order to determine if the connection is considered to have or not to have passed the integrity verification.

In some options, if Helium (or other tracer gas) quickly leaks out of the accumulating space, here the interior chamber 42, into the detection space of the detection chamber CH where helium partial pressure is measured (and possibly displayed on a screen), the profile of the helium partial pressure will be representative of the prompt increase in partial pressure. The analysis module 19 is thus suitable to confirm helium as detected is helium coming from the interior chamber 42. If only the fluid transfer system 200 is teste, it means that there exists a hole or defect at the coupling region of the fluid transfer assembly 200 under test, which cannot be considered leak-proof.

Conclusion about the integrity depends on early detection of the tracer gas after a pressure drop. More generally, it is understood that any tracer gas partial pressure increase or similar suitable tracer gas parameter is measured/detected in the detection space, in order to conclude if the connection passed the tracer gas integrity test.

The control unit 13 may be adapted to coordinate steps during a measuring cycle. Such test may be efficient to detect very small defects. In some embodiments, the systems having passed the test successfully are considered having no defect greater than a low size threshold, for example about 2 µm (two micrometers). Such testing apparatus will not be described in greater details as the solution is more particularly related to the sealing arrangement 100.

Of course, a gas source connecting step is typically performed after assembling the sealing arrangement 100 and after forming the connection around the first annular part 101, which may be a barbed nozzle 1*a*. Thus, the valve V5 such as shown in FIG. 6 or any similar valve for tracer gas injection typically remains in closed state before the assembling step involving the intermediate portion 1*c* and before the connection step involving the connecting part/barbed nozzle 1*a*. Such valve is open at an injection step for injecting the tracer gas G in the interior chamber 42, before an analyzing step performed by the analyzing module 19 associated to the sensor device 9.

Each bag/pouch 40, 40' of the assembly 18 can be tested with the fluid transfer assembly 200, using a vacuum chamber. A same vacuum chamber or different vacuum chambers may be used.

Of course, the evacuating step may be typically performed after the clamping of some hoses/tubes and injection step can start after evacuation of the tested zone/detection space of the detection chamber CH. The interior chamber 42 may be part of the interior volume of a whole arrangement/assembly 18 or circuit and clamps 3' (see FIG. 2A) may be used to delimit a smaller interior chamber as compared to the whole fluid capacity of the assembly 18.

After the test, a disconnection step may be performed, in which the supplying line or channel 5 is disconnected from the biopharmaceutical disposable/sterile system provided with the hose 11 and clamping by clamps (if any) is released. The fluid transfer assembly 200 as tested, if successfully tested, can be used for biopharmaceutical applications requiring high integrity level, for instance compliance with 2 µm test.

The continuous radial contact around the intermediate portion 1*c*, combined with a compression according to a radial direction is efficient for forming a gas-barrier.

While the above detailed embodiments show use of a source of pressurized helium 14, which typically contains helium (for instance helium with usual purity suitable for medical use), the amount of helium injected around the flexible bag 2 could possibly be added using a different kind of source, possibly using a gas mixture or helium without same level of purity.

The test method is appropriate for detecting a leak of micrometric size, even for high capacity bags 40, 40' present in the arrangement/assembly 18.

A leak test kit for testing a fluid fitting thus can be obtained, using the housing unit 2 as a compact built-in interior chamber end complement, without interfering with the connection under test. Also, when membranes are provided to cover the second opening O', they are still available after removing the housing unit 2.

Of course, the invention is not limited to the embodiments described above and provided only as examples. It encompasses the various modifications, alternative forms, and other variants conceivable to a skilled person within the context of the invention, and in particular any combinations of the various modes of operation described above, which may be taken separately or in combination.

For instance, the intermediate portion 1*c* is not necessarily a transition part between a gripping portion 105 and the end component 15, 15', as illustrated in the FIGS. 1 and 8. The gripping portion 105 or any other suitable portion, interposed between the attachment component 15, 15' and the barbed nozzle, can be received in the inner volume V, typically by extending beyond an annular contact region with a flexible material compressed or pinched by the housing unit 2. In particular, the sealing structure 4 does not necessarily include a ring R4, R4' resting on the connecting device 1, 1' at an annular recess thereof. In some embodiments, the gas-tight junction at the access passageway 20 may be obtained by a continuous annular contact of the housing unit 2 with the flexible material included in the hose end 11*a* (or tightly surrounding the hose end 11), provided this contact is obtained around the intermediate portion 1*c*.

The invention claimed is:

1. A sealing arrangement for use in detecting a detectable gas in a hermetically sealed detection chamber, the sealing arrangement comprising:
   - a housing unit provided with a first housing part a second housing part and an access passageway, the first housing part and the second housing part delimiting an inner volume of the housing unit in a closed state, the inner volume being accessible via the access passageway;
   - a connecting device, which comprises a tubular part extending from a first annular part to a second annular part, the tubular part delimiting a fluid passage and having an intermediate portion of annular shape arranged around the fluid passage, between the first annular part and the second annular part; and
   - a sealing structure adapted to form a gas-tight junction at the access passageway, by a continuous contact around the intermediate portion, when the second annular part is received in the inner volume in the closed state of the housing unit;

wherein the first annular part is configured to be overlapped by a flexible hose end, while the second annular part is provided with an attachment component, and wherein the housing unit is configured to receive the attachment component in the inner volume, so that gas escaping from the fluid passage via at least one gas permeable end included in the attachment component is hermetically kept in the inner volume.

2. The sealing arrangement according to claim 1, wherein the sealing structure comprises at least one piece that is sandwiched between a first rigid piece forming all or part of the first housing part and a second rigid piece forming all or part of the second housing part.

3. The sealing arrangement according to claim 1, wherein the sealing structure is resiliently deformable, and wherein the sealing arrangement further comprises clamping members arranged at a periphery of the housing unit, around the inner volume, for maintaining a compressed state of the sealing structure, by locking the closed state of the housing unit.

4. The sealing arrangement according to claim 1, wherein the first annular part is a barbed nozzle made of plastic.

5. The sealing arrangement according to claim 1, wherein the connecting device is provided with an annular recess, the intermediate portion extending at the annular recess, the sealing structure surrounding the intermediate portion by extending in the annular recess.

6. The sealing arrangement according to claim 1, wherein the first housing part and the second housing part are made of or include metallic material.

7. The sealing arrangement according to claim 1, wherein fluid communication between the inner volume and outside of the housing unit is only possible via the fluid passage, in the closed state of the housing unit.

8. The sealing arrangement according to claim 1, wherein the at least one gas permeable end included in the attachment component comprises an end opening that:
  belongs to the second annular part; and
  is covered by a gas permeable membrane.

9. The sealing arrangement according to claim 1, comprising:
  a flexible hose including the flexible hose end that overlaps the first annular part;
  a clamping collar configured to be permanently deformably crimped around a location of overlap between the flexible hose end and a shank part of the first annular part that is barbed, the shank part extending between a shoulder or abutment portion and a barb of the first annular part.

10. The sealing arrangement according to claim 1, wherein the housing unit is provided with a connector fitting, including metal, the connector fitting delimiting a communication channel that opens in the inner volume, outside the fluid passage.

11. A method of leakage monitoring a fluid transfer assembly for use in a biopharmaceutical assembly, by using the sealing arrangement according to claim 1, the method comprising,
  in a preparation phase:
    coupling the connecting device, which forms a first one of the two fluid receiving parts, to a hose to obtain a coupled state of the fluid transfer assembly, the coupling comprising inserting the first annular part as a male part inside the hose at a flexible hose end formed as a female part, the hose forming all or part of the second one of the two fluid receiving parts;
    delimiting an annular contact area at a coupling region where the flexible hose end overlaps on the first annular part;
    assembling the sealing arrangement so that the fluid passage selectively communicates with the internal volume of the housing unit, via an opening covered by a gas permeable membrane;
  and then in a test phase:
    injecting a tracer gas inside an accumulating space separated from a detection space by the annular contact area (SC), in order to accumulate said tracer gas in the fluid passage, the detection space being located inside a hermetically sealed detection chamber;
  whereby any escape from the tracer gas through a possible defect of the annular contact area can be detected in the detection space, by a tracer gas sensor device that is in fluid communication with the detection space.

12. An apparatus for use in detecting a detectable gas in a hermetically sealed detection chamber, the apparatus comprising:
  a sterilized container for positioning in the detection chamber, said container having a flexible body at least partially defining an interior chamber for receiving and holding the detectable gas in the absence of a leak;
  the sealing arrangement according to claim 1 for positioning in the detection chamber;
  a hose including the flexible hose end connected to the first annular part and allowing fluid communication between the at least one gas permeable end and the interior chamber;
  a sensor device associated with the detection chamber and capable of sensing the detectable gas external to the interior chamber, in a detection space of the detection chamber, as the result of the leak; and
  a pumping assembly for creating a pressure differential between the interior chamber and the detection chamber;
  wherein the housing unit and the sealing structure hermetically separate the inner volume, in which the attachment component having the at least one gas permeable end is received, from the detection space.

13. The apparatus according to claim 12, comprising a source of detectable gas and a valve associated to the source of detectable gas,
  wherein the connecting device and the flexible hose end are connected at a coupling region for forming a fluid transfer assembly,
  and wherein the interior chamber is configured to be filled in the detectable gas when the valve is in an open state, via an injection line that communicates with the fluid passage via the interior chamber.

14. The sealing arrangement according to claim 1, wherein the sealing structure comprises two deformable pieces each made of resilient plastic material.

15. The sealing arrangement according to claim 14, wherein the two deformable pieces of the sealing structure comprise:
  two substantially planar parts, parallel and joined to each other in the closed state, and
  a ring that is complementary to the two planar parts, the ring surrounding and enclosing the intermediate portion.

16. The sealing arrangement according to claim 14, wherein the sealing structure is provided with a ring distributed in the two deformable pieces.

* * * * *